(12) United States Patent
Foley et al.

(10) Patent No.: US 8,161,966 B2
(45) Date of Patent: Apr. 24, 2012

(54) RESPIRATORY MUSCLE ENDURANCE TRAINING DEVICE AND METHOD FOR THE USE THEREOF

(75) Inventors: Martin P. Foley, London (CA); Jerry R. Grychowski, Lake Zurich, IL (US)

(73) Assignee: Trudell Medical International, London, Ontario (CA)

( * ) Notice: Subject to any disclaimer, the term of this patent is extended or adjusted under 35 U.S.C. 154(b) by 1048 days.

(21) Appl. No.: 11/842,778

(22) Filed: Aug. 21, 2007

(65) Prior Publication Data

US 2008/0096728 A1      Apr. 24, 2008

(51) Int. Cl.
*A63B 23/00*      (2006.01)
(52) U.S. Cl. .............. 128/200.24; 128/200.12
(58) Field of Classification Search ............ 128/206.21, 128/207.13, 200.24, 204.18, 204.21, 200.25, 128/200.12, 205.12; 482/13
See application file for complete search history.

(56) References Cited

U.S. PATENT DOCUMENTS

| | | | |
|---|---|---|---|
| 2,007,330 A | 7/1935 | Hicks | |
| 2,304,033 A | 12/1942 | Shelton | |
| 2,321,256 A | 6/1943 | Shelton | |
| 3,455,294 A | 7/1969 | Adler et al. | |
| 3,863,914 A | 2/1975 | O'Connor | |
| 3,949,984 A | 4/1976 | Navara | |
| 4,192,301 A | 3/1980 | Hardwick | |
| 4,221,381 A | 9/1980 | Ericson | |
| 4,275,722 A | 6/1981 | Sorensen | |
| 4,291,704 A | 9/1981 | Petty et al. | |
| 4,301,810 A | 11/1981 | Belman | |
| 4,508,116 A | 4/1985 | Duncan et al. | |
| 4,627,432 A | 12/1986 | Newell et al. | |
| 4,628,926 A | 12/1986 | Duncan et al. | |
| 4,854,574 A * | 8/1989 | Larson et al. ................ | 482/13 |
| 4,938,210 A | 7/1990 | Shene | |
| 4,973,047 A | 11/1990 | Norell | |
| 5,103,854 A | 4/1992 | Bailey et al. | |
| 5,154,167 A | 10/1992 | Hepburn | |
| 5,165,393 A * | 11/1992 | Kawaguchi ............ | 128/200.24 |
| 5,245,991 A | 9/1993 | Kawaguchi | |
| 5,385,140 A | 1/1995 | Smith | |

(Continued)

FOREIGN PATENT DOCUMENTS

DE      199 12 337 C1      8/2000

(Continued)

OTHER PUBLICATIONS

Office Action (Non-Final) in U.S. Appl. No. 12/388,952, Foley et al., mailed Dec. 10, 2010, 5 pages.

(Continued)

*Primary Examiner* — Jerome w Donnelly
(74) *Attorney, Agent, or Firm* — Brinks Hofer Gilson & Lione (57) ABSTRACT

A respiratory muscle endurance training device (RMET) includes a chamber and a patient interface. In one implementation, one or both of a $CO_2$ sensor or a temperature sensor can be coupled to the chamber or patient interface to provide the user or caregiver with indicia about the $CO_2$ level in, or the temperature of, the chamber or patient interface, and/or the duration of use of the device. In another implementation, the RMET may have a fixed volume portion adjustable to contain a measured portion of a specific patient's inspiratory volume capacity. Methods of using the device are also provided.

10 Claims, 5 Drawing Sheets

U.S. PATENT DOCUMENTS

| | | | |
|---|---|---|---|
| 5,582,162 | A | 12/1996 | Petersson |
| 5,647,345 | A | 7/1997 | Saul |
| 5,740,793 | A | 4/1998 | Hodson et al. |
| 5,749,368 | A * | 5/1998 | Kase ............................ 600/533 |
| 5,755,640 | A | 5/1998 | Frolov et al. |
| 5,816,240 | A | 10/1998 | Komesaroff |
| 6,026,807 | A | 2/2000 | Puderbaugh et al. |
| 6,039,042 | A | 3/2000 | Sladek |
| 6,083,141 | A | 7/2000 | Hougen |
| 6,116,239 | A | 9/2000 | Volgyesi |
| 6,165,105 | A | 12/2000 | Boutellier et al. |
| 6,293,279 | B1 | 9/2001 | Schmidt et al. |
| 6,345,617 | B1 | 2/2002 | Engelbreth et al. |
| 6,390,090 | B1 | 5/2002 | Piper |
| 6,408,848 | B1 | 6/2002 | Feldman |
| 6,435,177 | B1 | 8/2002 | Schmidt et al. |
| 6,500,095 | B1 * | 12/2002 | Hougen ........................ 482/13 |
| 6,557,549 | B2 | 5/2003 | Schmidt et al. |
| 6,631,716 | B1 | 10/2003 | Robinson et al. |
| 6,848,443 | B2 | 2/2005 | Schmidt et al. |
| 6,880,557 | B2 | 4/2005 | Downey |
| 6,904,908 | B2 | 6/2005 | Bruce et al. |
| 2002/0069870 | A1 | 6/2002 | Farmer |
| 2002/0115533 | A1 | 8/2002 | Horstel et al. |
| 2004/0146842 | A1 | 7/2004 | Carlucci et al. |

FOREIGN PATENT DOCUMENTS

| | | |
|---|---|---|
| EP | 0 027 154 | 4/1981 |
| EP | 0 027 154 A | 4/1981 |
| EP | 0 372 148 A1 | 6/1990 |
| EP | 1 021 225 B1 | 4/1999 |
| EP | 1 485 157 B1 | 3/2003 |
| EP | 1 377 347 B1 | 1/2004 |
| GB | 2 238 728 A | 6/1991 |
| GB | 2 278 545 A | 12/1994 |
| WO | WO 01/39837 A1 | 6/2001 |
| WO | WO 02/081034 A2 | 10/2002 |
| WO | WO 2008/024375 A2 | 2/2008 |

OTHER PUBLICATIONS

International Search Report in International Application No. PCT/US2007/018527, dated Feb. 20, 2008, 4 pages.

Written Opinion in International Application No. PCT/US2007/018527, dated Feb. 20, 2008, 9 pages.

Koppers, M.D., Ralph J.H., Vos, M.D., Ph.D., Petra J.E., Boot, Ph.D., Cecile R.L., and Folgering, M.D., Ph.D., Hans Th.M., "Exercise Performance Improves in Patients With COPD due to Respiratory Muscle Endurance Training," Manuscript—Original Research COPD, American College of Chest Physicians (www.chestjournal.org/misc/reprints.shtml), Apr., 2006, pp. 886-892.

"FEMEN® $CO_2$ Indicator—Innovative Technology for $CO_2$ Indication," Engineered Medical Systems, Inc., Indianapolis, IN, USA, date unknown, 2 pages.

European Search Report in European Application No. 10 19 2608, mailed May 3, 2011, 6 pages.

Partial International Search Results for International Application No. PCT/US2009/034474, dated May 18, 2009, 2 pages.

International Search Report in International Application No. PCT/US2009/034474, dated Aug. 28, 2009, 8 pages.

Written Opinion of the International Searching Authority for International Application No. PCT/US2009/034474, dated Aug. 28, 2009, 8 pages.

International Preliminary Report on Patentability for International Application No. PCT/US2007/018527, dated Feb. 24, 2009, 9 pages.

International Preliminary Report on Patentability for International Application No. PCT/US2009/034474, dated Aug. 24, 2010, 7 pages.

U.S. Appl. No. 12/388,952 for "Respiratory Muscle Endurance Training Device and Method for the Use Thereof" filed Feb. 19, 2009, for Foley, et al.

* cited by examiner

RESPIRATORY MUSCLE ENDURANCE TRAINING DEVICE AND METHOD FOR THE USE THEREOF

CROSS-REFERENCE TO RELATED APPLICATION

This application claims the benefit of pending U.S. Application No. 60/839,040, filed Aug. 21, 2006, the entirety of which is incorporated herein by reference.

TECHNICAL FIELD

The present disclosure relates generally to a training device, and in particular, to a respiratory muscle endurance training device.

BACKGROUND

Patients with respiratory ailments, in particular patients with COPD (Chronic Obstructive Pulmonary Disease), have impaired exercise tolerance and diminished ventilatory efficiency. Various techniques have been developed to improve respiratory muscle endurance capacity. For example, one technique involves respiratory muscle training through the use of positive expiratory pressure devices, such as the AEROPEP PLUS valved holding chamber available from Trudell Medical International, the Assignee of the present application.

Another technique is referred to as Respiratory Muscle Endurance Training (RMET). Most current RMET techniques require complicated and expensive equipment, which limits widespread use. Alternatively, a portable tube has been developed for use by COPD patients, and has been effective in improving the endurance exercise capacity of the users.

SUMMARY

A respiratory muscle endurance training device includes a chamber and a patient interface. One or both of a $CO_2$ sensor or a temperature sensor can be coupled to the chamber or patient interface to provide the user or caregiver with indicia about the $CO_2$ level in, or the temperature of, the chamber or patient interface, and/or the duration of use of the device. In various embodiments, one-way inhalation and exhalation valves and flow indicators can also be associated with the chamber or patient interface.

In one aspect of the invention, a respiratory muscle endurance training device includes a patient interface for transferring a patient's exhaled or inhaled gases and a fixed volume chamber in communication with the patient interface, where the fixed volume chamber is sized to retain a portion of a patient's exhaled gases. A variable volume chamber in communication with the fixed volume chamber, where the variable volume chamber is configured to be responsive to the patient's exhaled or inhaled gases to move from a first position to a second position. A variable orifice may be positioned on the variable volume chamber to permit a desired amount of exhaled air to escape during exhalation and to receive a supply of air to replace the escaped exhaled air during inhalation.

Methods of using the device are also provided. In particular, the user inhales and exhales into the chamber. Over the course of a plurality of breathing cycles, the $CO_2$ level in the chamber increases, thereby increasing the work of breathing and exercising the user's lungs. In other embodiments, a visual or audible indicator which may be located on the housing of the device may provide flashes or beeps, respectively, to prompt a patient to inhale or exhale at each such indication. In yet other embodiments, a visual or audible indicator that is separate from the device may be used to assist a patient in establishing the desirable breathing pattern.

The various embodiments and aspects provide significant advantages over other respiratory muscle training devices. In particular, the training device is portable and the volume can be easily adjusted to accommodate different users, for example those with COPD, as well as athletes with healthy lungs. In addition, the user or care giver can quickly and easily assess the level or duration of use by way of various sensors, thereby providing additional feedback as to the proper use of the device.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION

Figure 1:
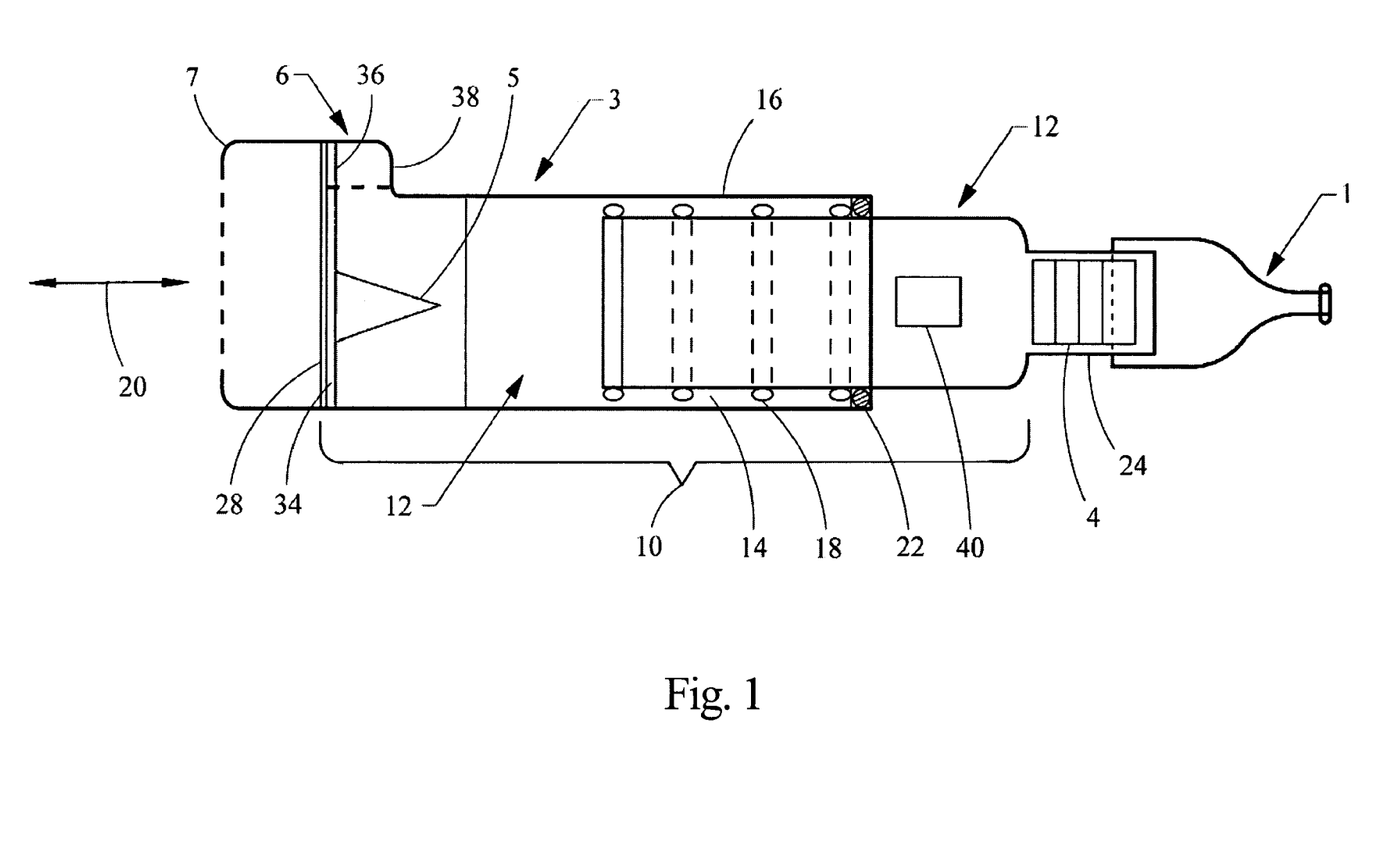
FIG. 1 is a side view of one embodiment of a respiratory muscle endurance training device.

Referring to FIG. 1, a respiratory muscle endurance training device includes a chamber 10, otherwise referred to as a spacer. In one embodiment, the chamber includes a first chamber component 2 and a second chamber component 3. In other embodiments, the chamber 10 is formed as a single unitary component. The first and second chambers define an interior volume 12 of the chamber.

In one embodiment, mating portions 14, 16 of the first and second chambers are configured as cylindrical portions or tubes, with the first chamber component 2 having an outer diameter shaped to fit within an inner diameter of the second chamber component 3. One or both of the chamber components are configured with circumferential ribs 18 and/or seals (shown in FIG. 1 on the first chamber component) that mate with the other chamber to substantially prevent exhaled air from escaping from the chamber interface. In one embodiment, the ribs 18 are spaced apart along the lengths of one or both of the chamber components so as to allow the chambers to be moved longitudinally in a longitudinal direction 20 relative to each other and then fixed at different lengths depending on the location of the ribs 18 and a mating shoulder 22 formed on the other chamber (shown in FIG. 1 as the second chamber component). The rings, or ribs, and shoulder are preferably integrally molded with the chambers, although they can also be affixed separately, e.g., as an o-ring. It should be understood that various detent mechanisms, including springs, tabs, etc. can be used to index the first chamber component relative to the second chamber component. Of course, it should be understood that the chambers can also be infinitely adjustable without any set detents, for example with a simple friction fit between the chamber components.

When adjusted, the overall interior volume 12 of the chamber 10 can be adjusted. For example, the interior volume 12 of the chamber can be adjusted from between about 500 cc to about 4000 cc. The chamber volume is adjusted depending on various predetermined characteristics of the user, such as peak expiratory flow. In this way, the interior volume 12 can be adjusted to reduce or increase the total exhaled volume of expired gases captured inside the chamber 10.

The first chamber component 2 includes an output end 24 that is coupled to a patient interface 1. It should be understood that the terms "coupling," "coupled," and variations thereof, mean directly or indirectly, and can include for example a patient interface in-molded with the first chamber at an output end thereof. The patient interface can be configured, without limitation, as a mask, a mouthpiece, a ventilator tube, etc. The term "output" merely refers to the fact that gas or air moves through or from the chamber to the patient interface during inhalation, notwithstanding that gas or air moves from the patient interface into the chamber during exhalation. The term "end" refers to a portion of the chamber that has an opening through which the gas or air moves, and can refer, for example, to a location on a spherical chamber having such an opening, with that portion of the sphere forming the "end."

The second chamber component 3 includes an input end 28, wherein air or gas flows into the chamber 10. The chamber preferably includes a one-way inhalation valve 5 that allows ambient air, or aerosol from an aerosol delivery device, to flow in a one-way direction through the input end 28 of the second chamber component and into the interior volume 12. During an exhalation sequence of the user, an exhalation valve 34 opens to allow exhaled gases to escape to the ambient air. The inhalation valve 5 is preferably configured as a duckbill valve, although other valves such as slit petal valves, center post valves, valves having a central opening with a peripheral sealing edge, etc. would also work. One acceptable valve is the valve used in the AEROPEP PLUS device, available from Trudell Medical International.

The exhalation valve 34 is preferably formed around a periphery of the inhalation valve. The second chamber 3 also includes a flow indicator 36, formed as a thin flexible member disposed in a viewing portion 38 formed on the second chamber, or as part of a valve cap 6. The flow indicator is configured to move during inhalation or exhalation to provide indicia to the user or caregiver that an adequate flow is being generated in the device. Various embodiments of the flow indicator and inhalation and exhalation valves are disclosed for example and without limitation in U.S. Pat. No. 6,904,908, assigned to Trudell Medical International, London, Ontario, Canada, the entire disclosure of which is hereby incorporated herein by reference. Examples of various aerosol delivery systems and valve arrangements are disclosed in U.S. Pat. Nos. 4,627,432, 5,385,140 5,582,162, 5,740,793, 5,816,240, 6,026,807, 6,039,042, 6,116,239, 6,293,279, 6,345,617, and 6,435,177, the entire contents of each of which are incorporated herein by reference. A valve chamber 7 is coupled to the input end of the second chamber. The valve chamber isolates and protects the valves from being contaminated or damaged, and further provides for coupling to a substance delivery device such as a tube or an aerosol delivery device.

The chamber 10, for example the first chamber component 2 and/or the patient interface 1, is configured with a $CO_2$ sensor 4, for example and without limitation a $CO_2$ Fenem colormetric indicator available from Engineering Medical Systems, located in Indianapolis, Ind. The $CO_2$ indicator 4 provides visual feedback to the user and/or caregiver as to what the $CO_2$ level is in the chamber 10, or the interior spaced defined by the chamber 10 and the patient interface 1, to ensure that the $CO_2$ level is sufficient to achieve the intended therapeutic benefit. As shown in FIG. 1, the sensor 4 is located at the output end of the chamber 10 adjacent the patient interface 1, or at the juncture of those components, whether formed integrally or separately. Of course, it should be understood that the sensor 4 can be located directly on or in the patient interface 1, or on or in either of the first and second chamber components 2, 3.

The expendable $CO_2$ indicator 4 is configured with user indicia to indicate the level of $CO_2$ in the chamber or interior. The indicator 4 includes a litmus paper with a chemical paper having a chemical material that reacts to the $CO_2$ concentration in a gas. For example and without limitation, the color purple indicates an atmospheric concentration of $CO_2$ molecules less than 0.03%. The color changes to a tan color at 2.0% $CO_2$ in the gas. The color yellow indicates 5.0% or more $CO_2$ concentration. At this level, the patient is re-inhaling expired gases (or dead space gases) to increase the concentration of $CO_2$ in the lungs of the user, which encourages the user to inhale deeper, thereby exercising the lung muscles to expand beyond their normal condition. The sensor and indicator 4 can be used to determine the $CO_2$ level, or the length of the time the user has been using the device. After use, the indicator 4 holds the reading for a period of time, so that a caregiver who is temporarily absent can get a reading after the use cycle is completed. Eventually the indicator will reset by returning to its original color scheme, such that it can be used again. The device is compact and lightweight, and is thus very portable.

The device can also be configured with a temperature sensor 40, such as a thermochromic liquid crystals strip, available from Hallcrest Inc., Glenview Ill. The temperature sensor 40 is secured to the outside (or inside) of one of the chamber or user interface. A sensor can also be configured to measure the actual gas/air temperature inside the chamber. In one implementation, the temperature sensor 40 may utilize cholestric liquid crystals (CLC). The temperature of the CLC is initially at room temperature. As the user successively breathes (inhales/exhales) through the device, the CLC will expand and contract depending on the temperature. Depending on the temperature, the color of the indicator will change, which also is indicative of, and can be correlated with, the length of time the user has been breathing through the device.

In one embodiment, an analog product line is used, which exhibits a line that moves throughout the temperature cycle and provides a direct correlation to the elapsed time of use. The temperature indicator can be configured to provide for an indication of temperature at least in a range from room temperature to slightly below the body temperature of the user, e.g., 37 degrees centigrade. A secondary temporal (e.g., minute) indicator can be located adjacent to the temperature indicator to provide an indication of how long the user has been using the device, with the temperature being correlated with the elapsed time. Again, the indicator can be configured to hold a reading, and then reset for subsequent and repeated use.

The training device can be coupled to an aerosol delivery device (not shown), such as a nebulizer or metered dose inhaler, to deliver medication to the user through the chamber and patient interface. In this way, the device performs two (2) functions, (1) respiratory muscle endurance training and (2) treatment for respiratory ailments or diseases such as COPD or asthma. In one embodiment, the metered dose inhaler is engaged through an opening formed in the valve chamber 7.

The materials used to manufacture the device may be the same as those used to make the AEROCHAMBER holding chambers available from Trudell Medical International of London, Ontario, Canada, which chambers are disclosed in the patents referenced and incorporated by reference above.

The diameter of the chambers 10, 2, 3 can range from between about 1 inch to about 6 inches. Although shown as cylindrical shapes, it should be understood that other cross-sectional shapes would also be suitable, including elliptical and rectangular shapes, although for devices also used for aerosol delivery, a cylindrical or elliptical shape is preferred to minimize impaction and loss of medication prior to reaching the patient.

An alternative embodiment of a respiratory muscle endurance training (RMET) system 50 is illustrated in FIGS. 2-5. In this embodiment, a tube 52 is connectable with a chamber which may have a fixed volume portion 54 defined by a housing 56. A flexible bellows 58 defines an adjustable volume portion 60. The tube 52 may be of a diameter ranging from 22 mm to 40 mm that provides a dead space volume (also referred to as rebreathing gas) of between 10 cubic centimeters (cc) to 40 cc per inch. The length may be varied between 10 inches to 36 inches in one embodiment. The tube 52 may be corrugated tubing made of polyvinyl chloride (PVC) and have markings every six inches for reference when cutting to a desired length. The fixed volume portion 54 defined by the housing 56 may be manufactured in two sections to enclose 1600 cc, however it may also be produced to have a volume in a range from 500 cc to 1600 cc in order to cover an expected range of patients from the small and thin to the large or obese.

Figure 2:
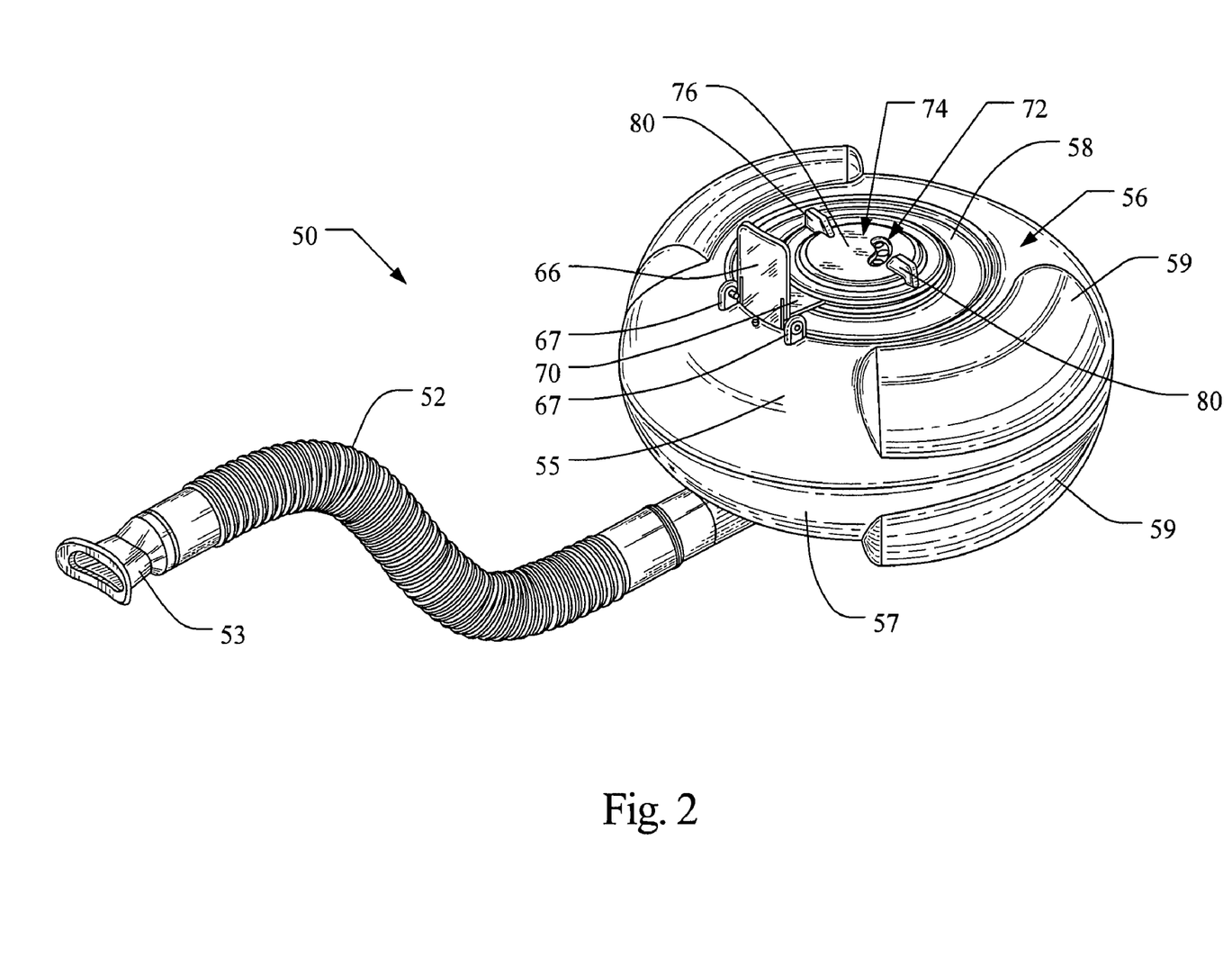
FIG. 2 is a perspective view of an alternative embodiment of the respiratory muscle endurance training device of FIG. 1.
Figure 3:
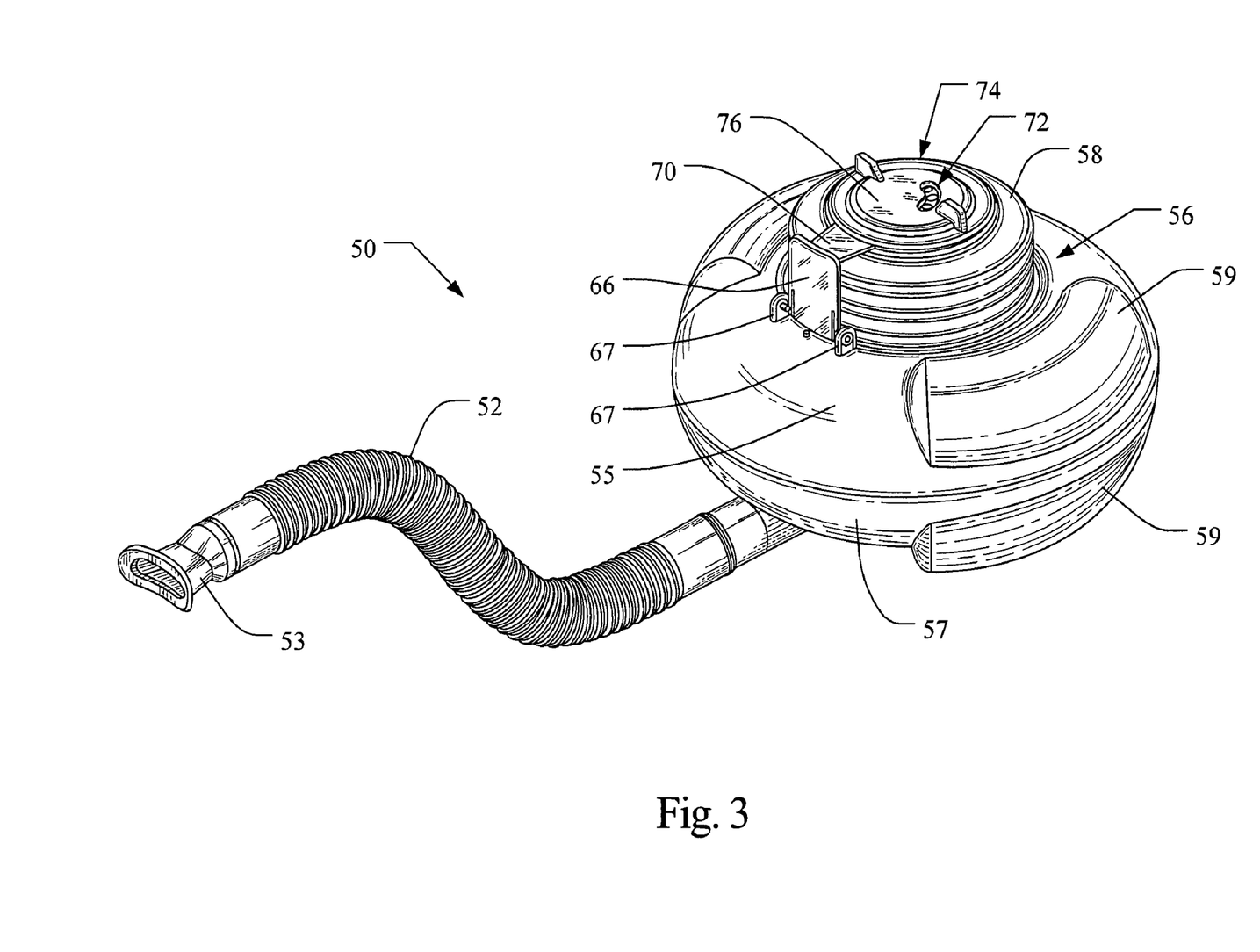
FIG. 3 is a perspective view of the device of FIG. 2 during exhalation with raised bellows.
Figure 4:
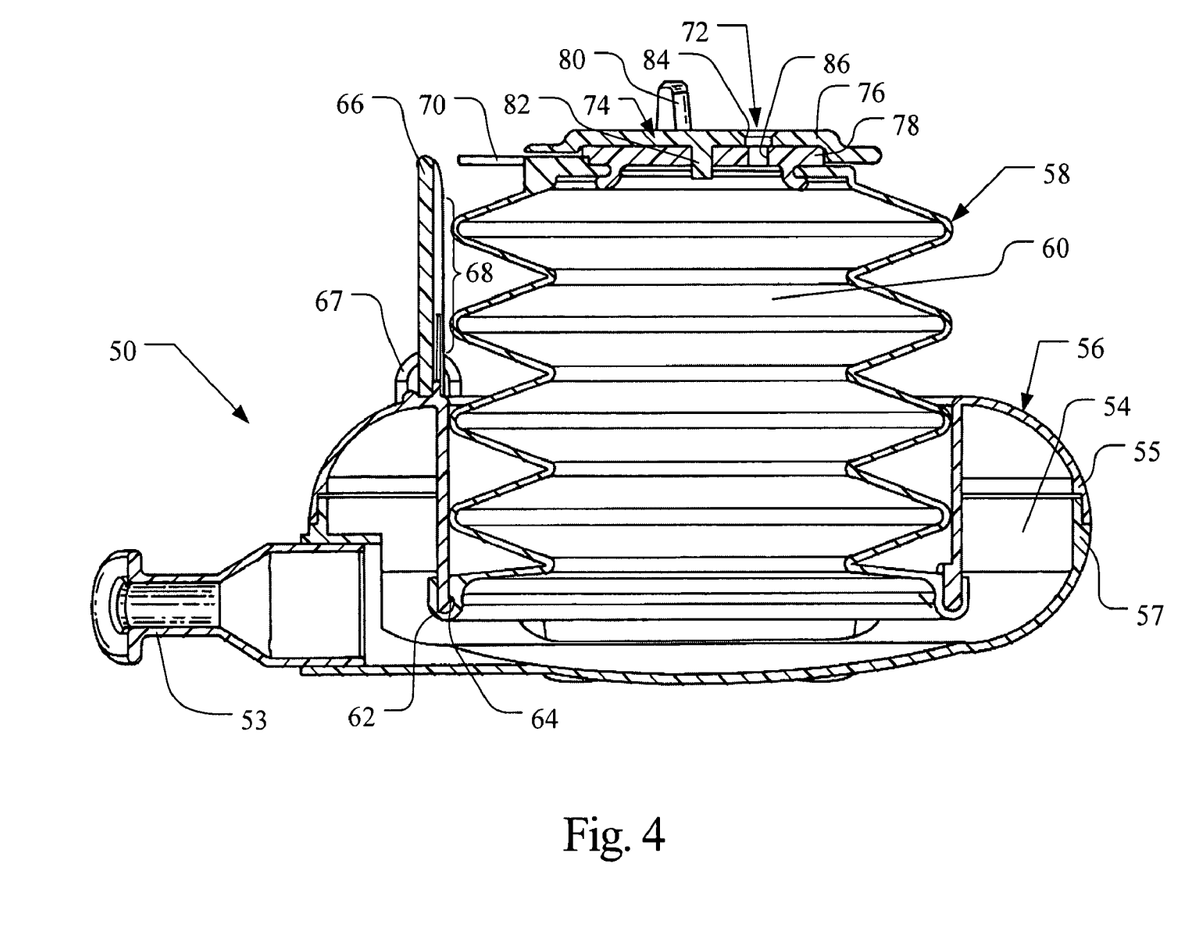
FIG. 4 is a cross-sectional view of the device of FIG. 3 without a flexible tube.

The housing 56 may be constructed from a polypropylene material or any of a number of other molded or formable materials. The housing may be manufactured in two halves 55, 57 that are friction fit together, glued, welded or connected using any of a number of know connection techniques. Also, the housing 56 may be fashioned in any of a number of shapes having a desired fixed volume. Hand rests 59, which may also be used as device resting pads, may be included on the housing 56. The bellows 58 may be manufactured from a silicone or other flexible material and connected with the housing 56 at a seal defined by a rim 62 on the housing 56 and a receiving groove 64 on the end of the bellows 58 that is sized to sealably grip the rim 62. In other embodiments, the bellows may be replaced with a balloon or other expandable body suitable for accommodating variable volumes. In the implementation of FIGS. 2-4, the housing 56 may have a diameter of 6 inches and a height of 3.5 inches. Other sizes may be fabricated depending on the desired volume of gases.

As best shown in FIG. 2, the bellows 58 may be contained within the housing 56 when no breathing is taking place using the system 50. FIGS. 2-3 illustrate the RMET system 50 with the bellows extended as a patient exhales. A volume reference member 66 having a scale 68 applied thereto or embedded therein may be mounted on the housing 56. The scale may be a linear scale such as a scale indicating increments of cc's, for example 100 cc increments from 0 to 500 cc. In one embodiment, the volume reference member 66 is foldable against the housing 56 by hinges 67 on the housing to permit a compact profile when not in use. An indicator 70 connected with the bellows 58 moves with the bellows 58 during breathing so that its position adjacent the volume reference member 66 on the housing 56 will provide information relating to the volume for each patient breath. FIG. 2 illustrates the RMET system 50 when the bellows 58 are fully retracted, such as when the device is at rest or a patient is inhaling. FIGS. 3-4 illustrate the system 50 with bellows 58 extended during patient exhalation.

The cap 74 on the bellows 58 defines a variable orifice 72 which may control the upper movement of the bellows 58 and define the final volume of the adjustable volume portion 60. The variable orifice 72 is set to allow excess exhaled gases to depart from the system to help prevent the patient from inhaling more than a desired percentage of the exhaled gases. In one embodiment, 60% of exhaled gases are desired for inhalation (rebreathing). In the RMET system 50 of FIGS. 2-4, the variable orifice 72 also acts to allow fresh, inspired gases to enter into the system 50 when the patient inhales more than the volume contained in the system 50. In this manner, the additional 40% of gases necessary after the 60% of exhaled gases have been inhaled may be breathed in. Preferably, there are no valves in the variable orifice 72 in order to allow the gases to flow freely through the system. By adjusting the resistance of the variable orifice 72 to flow on exhalation, the height of the bellows is adjusted during exhalation and the desired mix of exhaled and fresh gases may be selected (in this example 60/40).

Figure 5:
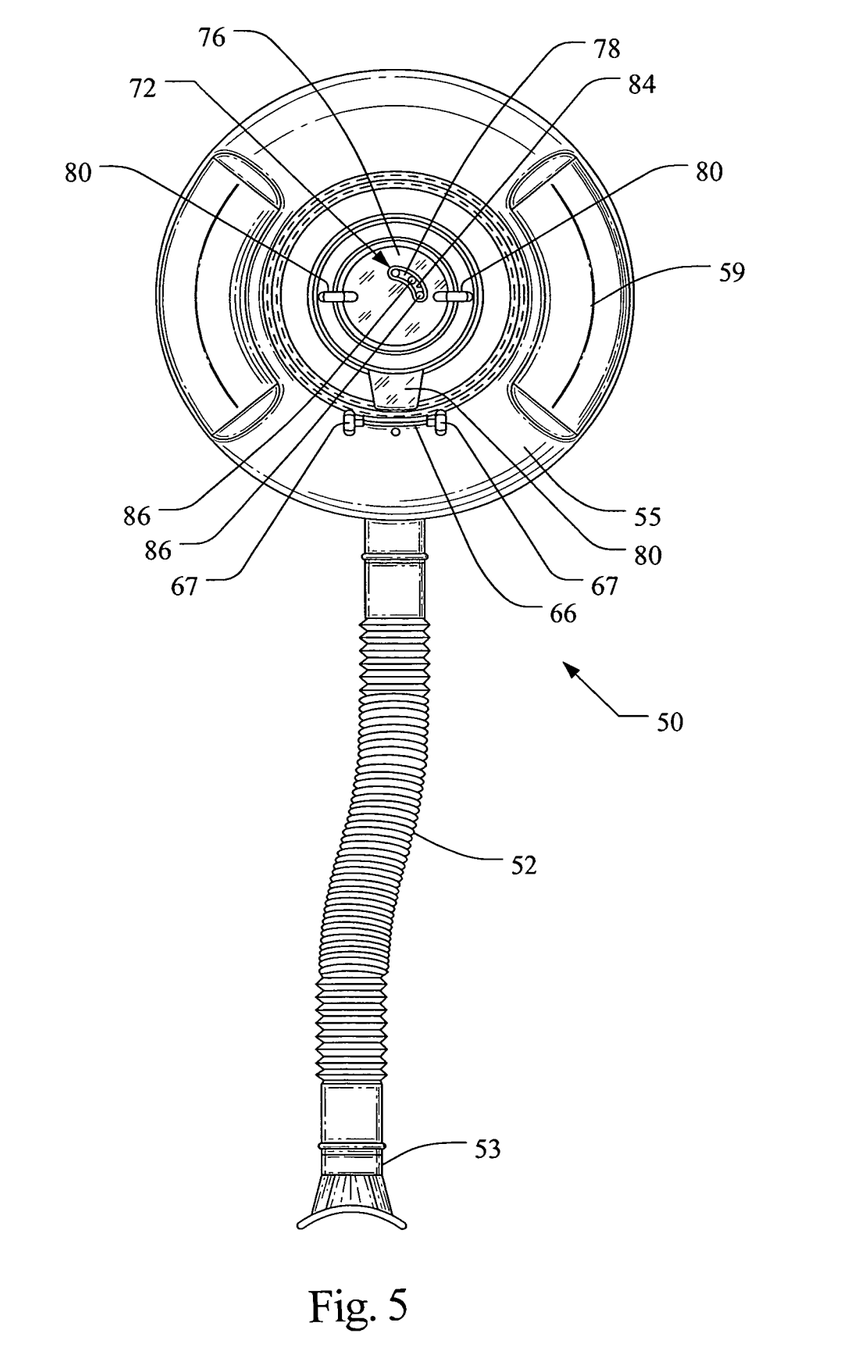
FIG. 5 is a top view of the device of FIGS. 2-3.

Referring to FIGS. 4-5, the variable orifice 72 may be formed by overlapping portions, where an upper portion 76 has an opening 84 that may be rotated with respect to an underlying portion 78 to selectively expose all or a portion of one or more openings 86 in the underlying portion. The variable orifice 72 may be adjusted by pushing against grips 80 extending out from the upper portion so that the upper portion will rotate about a central axis. By pushing against the grips 80 and turning the upper portion 76 with respect to the lower portion 78 about a central axis 82, the opening 84 in upper portion 76 may be aligned with one or more openings 86 in the lower portion 78. Although a rotatable arrangement is illustrated, other arrangements to vary an opening size are contemplated.

In operation, a patient first exhales into the patient interface, which may be a mouthpiece 53, mask or other interface on the end of the corrugated tubing 52. Upon the subsequent inhalation, the patient will inhale expired gases located in the corrugated tubing 52, the fixed volume portion 54 and the adjustable volume portion 60, in addition to any additional fresh gas (such as ambient air) entering into the system through the variable orifice 72 on the flexible bellows 58. The amount of exhaled gases may be set to be approximately 60% of the maximum voluntarily ventilation (MVV). To calculate how the level of ventilation may be set to approximately 60% of MVV, one may multiply 35×FEV1 (forced expiratory volume in the first second). This results in the relationship of 60% MVV=0.6×35×FEV1. The dead space of the RMET system 50, in other words the amount of volume for holding exhaled gases, may be adjusted to 60% of the patient's inspiratory vital capacity (IVC). The breathing pattern of the patient must be set above the normal breaths per minute, which is generally 12 to 15 breaths per minute. A breathing pattern between 16 to 30 breaths per minute may be suitable depending on the patient. In the embodiments as described herein, the breathing pattern is preferably 20 breaths per minute. The embodiments as described herein may comprise a visual or audible indicator to assist the patient in establishing the desirable breathing pattern. For example, where the desired breathing pattern is 20 breaths per minute a visual indicator, such as a light, would flash on and off every 3 seconds prompting the patient to inhale every time the light is on or every time the light turns off. The visual or audible indicator could be located adjacent the volume reference member 66. Although a mouthpiece 53 may be directly connected with the housing 56 as shown in FIG. 4, the tubing 52 shown in FIGS. 2-3 permit greater flexibility in customizing the amount of exhaled air retained in the system 50.

Assuming that, on average, a COPD patient's IVC is approximately 3.3 liters, 60% of 3.3 liters is approximately 2 liters. To achieve this capacity with the RMET system 50, an accumulation of a fixed volume plus a variable volume is used. The fixed volume with a flexible tubing 52 (120 cc to 240 cc) plus a fixed volume portion 54 of 1600 cc defined by the housing 56, along with a bellows 58 adjustable between approximately 0 cc to 400 cc accounts for the 60% of the IVC. During exhalation, 40% of the expired volume of gases may be expelled through the variable orifice 72 in the bellows 58. During inhalation, the patient may inhale the exhaled volume of gases in the system 50 and inhale the remaining 40% of gases necessary to complete the IVC through the variable orifice 72 on the bellows 58. To adjust the volume of expired gases collected from the patient, it is possible to reduce the length of the corrugated tube and reduce the fixed volume of gas in the device.

The patient observes the movement of the indicator 70 against the scale 68 on the housing to determine that the 60% volume of the patient's IVC has been reached. A separate or integrated timing device (not shown), such as a mechanical or electronic timer emitting an audible and/or visible signal, can assist the patient to perform a breathing program at a sufficient rate of breaths per minute. It is contemplated that the initial setting of the RMET system 50 to 60% of a patient's specific IVC may be made by a caregiver. The caregiver or patient may, for example, use a pulmonary function machine to determine the patient's FEV1 which can then be used to calculate the patient's MVV and ultimately 60% of the IVC.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A respiratory muscle endurance training device comprising:
   an adjustable chamber adjustable between at least a first interior volume and a second interior volume, said adjustable chamber comprising an output end, an input end spaced from said output end and a one-way inhalation valve disposed proximate said input end; and
   a patient interface connected to said output end of said chamber.

2. The respiratory muscle endurance training device of claim 1 further comprising a one-way exhalation valve disposed proximate said input end of said chamber.

3. The respiratory muscle endurance training device of claim 1 further comprising a flow indicator moveable in response to one or both of an inhalation and exhalation.

4. The respiratory muscle endurance training device of claim 1 wherein said adjustable chamber comprises first and second tubular members, wherein said first and second tubular members interface and are moveable relative to each other between at least a first and second position so as to define said first and second interior volumes.

5. A respiratory muscle endurance training device comprising:
   an adjustable chamber adjustable between at least a first interior volume and a second interior volume, said adjustable chamber comprising an output end;
   a patient interface connected to said output end of said chamber; and
   a $CO_2$ sensor coupled to at least one of said chamber and said patient interface.

6. The respiratory muscle endurance training device of claim 5 wherein said $CO_2$ sensor comprises a Fenem colorimetic indicator disposed on an interior of one of said chamber and said patient interface.

7. A respiratory muscle endurance training device comprising:
   an adjustable chamber adjustable between at least a first interior volume and a second interior volume, said adjustable chamber comprising an output end;
   a patient interface connected to said output end of said chamber; and
   a temperature sensor coupled to at least one of said chamber and said patient interface.

8. The respirator muscle endurance training device of claim 7 wherein said temperature sensor is mounted on an exterior of said at least one of said chamber and said patient interface.

9. A respiratory muscle endurance training device comprising:
   a chamber comprising an output end;
   a patient interface connected to said output end of said chamber, said patient interface and said chamber defining an interior space; and
   a $CO_2$ sensor interfacing with said interior space and comprising user indicia adapted to indicate at least one of a level of $CO_2$ in said interior space or a length of time of usage by a user.

10. A respiratory muscle endurance training device comprising:
    a chamber comprising an output end;
    a patient interface connected to said output end of said chamber, said patient interface and said chamber defining an interior space; and
    a temperature sensor coupled to at least one of said chamber and said patient interface and comprising user indicia adapted to indicate at least one of a temperature of said interior space, said chamber and said patient interface or a length of time of usage by a user.

* * * * *

UNITED STATES PATENT AND TRADEMARK OFFICE
CERTIFICATE OF CORRECTION

| | | |
|---|---|---|
| PATENT NO. | : 8,161,966 B2 | Page 1 of 1 |
| APPLICATION NO. | : 11/842778 | |
| DATED | : April 24, 2012 | |
| INVENTOR(S) | : Martin P. Foley et al. | |

It is certified that error appears in the above-identified patent and that said Letters Patent is hereby corrected as shown below:

On the Title Page

Left column, after item (65), insert a new item as follows:

-- Related U.S. Application Data

Provisional application No. 60/839,040, filed on August 21, 2006. --.

Signed and Sealed this
Thirty-first Day of July, 2012

David J. Kappos
*Director of the United States Patent and Trademark Office*